US00RE34394E

United States Patent [19]

Bunting

[11] E Patent Number: Re. 34,394

[45] Reissued Date of Patent: Sep. 28, 1993

[54] METHOD AND COMPOSITION FOR DOUBLE RECEPTOR, SPECIFIC BINDING ASSAYS

[75] Inventor: James R. Bunting, Washington, D.C.

[73] Assignee: Baxter Diagnostics Inc., Deerfield, Ill.

[21] Appl. No.: 629,020

[22] Filed: Dec. 18, 1990

Related U.S. Patent Documents

Reissue of:

[64] Patent No.: 4,271,140
Issued: Jun. 2, 1981
Appl. No.: 930,130
Filed: Aug. 1, 1978

U.S. Applications:

[63] Continuation of Ser. No. 353,814, May 2, 1989, and a continuation-in-part of Ser. No. 871,478, Jan. 23, 1978, abandoned.

[51] Int. Cl.[5] ..... G01N 33/53; G01N 33/566; G01N 33/567; C12Q 1/00

[52] U.S. Cl. ..... 436/500; 435/5; 435/7.1; 435/7.92; 435/7.94; 436/501; 436/503; 436/505; 436/518; 436/531; 436/544; 436/545; 436/546; 436/800; 436/810; 436/815; 436/820; 436/822; 436/823; 436/824

[58] Field of Search ..... 436/500, 501, 503, 505, 436/518, 531, 544, 545, 546, 800, 810, 815, 820, 822, 823, 824; 435/5, 7.1, 7.92, 7.94

[56] References Cited

U.S. PATENT DOCUMENTS

| | | | |
|---|---|---|---|
| 3,646,346 | 2/1972 | Catt . | |
| 3,799,740 | 3/1974 | Mincey . | |
| 3,935,074 | 1/1976 | Rubenstein et al. . | |
| 3,940,475 | 2/1976 | Gross . | |
| 3,949,064 | 4/1976 | Bornstein et al. . | |
| 3,996,345 | 12/1976 | Ulman et al. . | |
| 4,000,252 | 12/1976 | Kosak . | |
| 4,011,308 | 3/1977 | Giaever . | |
| 4,020,151 | 4/1977 | Bolz et al. . | |
| 4,039,652 | 8/1977 | Adams et al. . | |
| 4,041,146 | 8/1977 | Giaever . | |
| 4,053,284 | 10/1977 | Posch . | |
| 4,055,633 | 10/1977 | Goldstein . | |
| 4,092,408 | 5/1978 | Litt . | |
| 4,108,975 | 8/1978 | Hales . | |
| 4,108,976 | 8/1978 | Reese . | |
| 4,120,945 | 10/1978 | Gutcho et al. . | |
| 4,134,792 | 1/1979 | Boguslaski et al. | 435/7 |
| 4,185,084 | 1/1980 | Mochida et al. . | |
| 4,208,479 | 6/1980 | Zuk et al. | 435/7 |
| 4,233,401 | 11/1980 | Yoshida et al. | 435/7 |
| 4,235,960 | 11/1980 | Sasse et al. . | |
| 4,243,749 | 1/1981 | Sadeh et al. . | |
| 4,343,896 | 8/1982 | Wolters et al. . | |

FOREIGN PATENT DOCUMENTS

| | | |
|---|---|---|
| 2744835 | 4/1978 | Fed. Rep. of Germany . |
| 1552607 | of 0000 | United Kingdom . |
| 1460631 | 1/1977 | United Kingdom . |

OTHER PUBLICATIONS

Wofsy, L. et al., Hapten-Sandwich Labeling, I. A General Procedure for Simultaneous Labeling of Multiple Cell Surface Antigens for Flourescence and Electron Microscopy. *J. Exp. Med.* 140:523-37 (1974).

(List continued on next page.)

*Primary Examiner*—Christine M. Nucker
*Assistant Examiner*—David R. Preston
*Attorney, Agent, or Firm*—Patterson & Keough

[57] ABSTRACT

The performance of double receptor, specific binding assays is improved by use of a receptor complex having the structure $$A_{BL}(BL)_nA_1$$

wherein BL is a binding ligand, $A_{BL}$ is a receptor specific for binding ligand, $A_1$ is a receptor, BL is covalently bonded to $A_1$ and $A_{BL}$ is reversibly bonded to BL. Generally $A_{BL}$ is absorbed onto an insoluble surface and $A_1$ is an antibody to the substance being assayed. The complex has particular utility in coated tube and rechargeable radioimmunoassay systems.

46 Claims, No Drawings

OTHER PUBLICATIONS

Nemanic, M. K. et al., Hapten-Sandwich Labeling. II. Imunospecific Attachment of Cell Surface Markers Suitable for Scanning Electron Microscopy. *J. Cell Biol.* 64:311-21 (1975).

Gurvich et al., 203 (4945): pp. 648-649 (1964).

Vector Laboratories Catalogue, issued about Mar. 1978.

Woodhead et al., Brit. Med. Bull, 30(1), pp. 44-49, 1974.

Heitzmann et al., Proc. Nat. Acad. Sci. U.S.A., 71(9), pp. 3537-3541 (1974).

Cuatrecasas et al., Ann. Rev. Biochem., 40:259, (1971).

Beck et al., Biochem J., 145 (1975), pp. 607-616.

Wilchek, M and Goreki, M., A New Approach for the Isolation of Biologically Active Compounds by Affinity Chromatography: Isolation of Trypsin, *FEBS LETTERS* 31 (1), pp. 149-152 (1973).

Bayer and Wilchek, The Avidin-Biotin Complex as a Tool in Molecular Biology, *Trends Biochem.*, pp. N257-N259, Nov. 1978.

Murphy, Immunoaffinity Chromatography, *Biochem. Soc. Trans.*, vol. 2, pp. 1298-1303 (1974).

Murphy et al., Avoidance of Strongly Chaotropic Eluents for Immunoaffinity Chromatography by Chemical Modification of Immobilized Ligand, *Biochemica et Biophysica Acta*, 420, pp. 87-96 (1976).

Wilchek and Hexter, The Purification of Biologically Active Compounds by Affinity Chromatography, *Methods of Biochemical Analysis*, vol. 23, pp. 347 et seq. (1976).

Choi, et al., *J. Experimental Medicine*, 139, pp. 761-766 (1974).

Heggeness, et al., Use of the Avidin-Biotin Complex for the Localization of Actin and Myosin with Fluorescence Microscopy, *J. Cell Biology* 73 pp. 783-788 (1977).

Manning, et al., A New Method of in situ Hybridization, Chromosoma, (Berl.) 53, pp. 107-117 (1975).

Hoffman et al., An Approach to the Targeted Attachment of Peptides and Proteins to Solid Supports, *Proc. Nat'l Acad. Sci. U.S.A.* 73 (10), pp. 3516-3518 (1976).

Manning et al., A Method for Gene Enrichment Based on the Avidin-Biotin Interaction. Application to the Drosophila Ribosomal RNA Genes, *Biochemistry*, 16(7), pp. 1364-1370 (1977).

Burd et al., Specific Protein-Binding Reactions Monitored by Enzymatic Hydrolysis of Ligand-Fluorescent Dye Conjugates, *Anal. Biochem*, 77, pp. 56-67 (1977).

"Immunohistochemical Localization of Melatonin in the Rat Harderian Gland" by G. A. Bubenik et al., J. Histochem. Cytochem., vol. 24, No. 11, pp. 1173-1177, 1976.

"Immunohistological Localization of N-Acetylindole-Alkylamines in Pineal Gland, Retina and Cerebellum" by Bubenik et al., Brain Research, 81 (1974) 233-242.

"Demonstration of a Chorionic Gonadotropin-Like Substance in Rabbit Morulae" by Asch et al., Fert. Ster., vol. 29, No. 4, Apr. 1978, pp. 444-446.

"Immunoflourescence Studies On Gonadotropin Releasing Hormone (GRH) in The Fore-Brain and the Neurohypophysis of the Green Frog, Rana osculenta L." by H. J. Th. Goos et al., Cell Tiss. Res. 168, 325—333 (1976).

"Immunocytochemical Localization of Secretory Proteins In Bovine Pancreatic Exocrine Cells" by J. P. Kraehenbuhl et al., The Journal of Cell Biology, vol. 72, 1977, pp. 406-423.

Hales, Immunological Techniques in Diabetes Research, Diabetologia, 8, 229-235 (1972).

Steadman's Medical Dictionary, p. 1133.

"Isolation of Soluble Immune Complexes by Affinity Chromatography Using Staphylococcal Protein A-Sepharose As Substrate" by F. Chenais et al., Journal of Immunological Methods, 18 (1977) pp. 183-192.

"Rapid Isolation Of Antigens From Cells With A Staphylococcal Protein A-Antibody Adsorbent: Parameters Of The Interaction of Antibody-Antigen Complexes With Protein A": by S. W. Kessler, The Journal of Immunology, vol. 115, No. 6, Dec. 1975.

"Simplified Radioimmunoassay for Viral Antigens: Use of Staphylococcus aureus as an Adsorbent for Antigen-Antibody Complexes: Brief Communication" by E. PremkumarReddy et al., J. Natl Cancer Institute, vol. 58, No. 6, Jun. 1977, pp. 1859-1861.

"Labelled Antibodies and Immunological Assay Systems" by Miles et al., Nature, vol. 219, Jul. 13, 1968, pp. 186-189.

Weintraub, *Biochemical and Biophysical Research Communications*, 39, 83-88 (1970).

Robbins et al., *Methods in Enzymology*, 34, 703-722 (1974).

Bunting, *Clinical Chemistry*, 24, Abstract 329 (Jun. 1978).

Robbins, et al., "Immunoadsorbents," *Clinical Chemistry*, 22, 1243-1255 (1976).

Bayer et al., *FEBS LETTERS*, 68, 240-244 (1976).

METHOD AND COMPOSITION FOR DOUBLE RECEPTOR, SPECIFIC BINDING ASSAYS

Matter enclosed in heavy brackets [ ] appears in the original patent but forms no part of this reissue specification; matter printed in italics indicates the additions made by reissue.

CROSS-REFERENCE TO RELATED APPLICATION

This is a continuation of Ser. No. 353,814 filed May 2, 1989, as a reissue application of U.S. Pat. No. 4,271,140, which is a continuation-in-part of U.S. patent application Ser. No. 871,478 filed Jan. 23, 1978, abandoned.

BACKGROUND OF THE INVENTION

This invention relates to specific binding assays in which two receptors or binding partners are employed. In such assays a first receptor is bound by a second receptor, with the first receptor being capable of reversibly binding either a ligand or, still further, another receptor to the exclusion of structurally related substances. For the purposes of this invention such assays will be termed double receptor specific binding assays.

Receptors are generally proteins, although other substances having reversible specific binding affinity for a ligand or for a labelled analogue thereof are equally useful. The most commonly used receptors are antibodies because they can be raised to bind any desired ligand. However, other binding proteins are included within the meaning of receptor, e.g., intrinsic factor, thyroxine binding globulin, cortisol binding protein, folate binding protein and membrane-associated specific receptor proteins. Receptors also may include low molecular weight substances such as dyes or amino acids that are capable of binding to proteins. As a general rule, receptors are the larger of the two components of a binding pair. However, for the purposes of this invention a receptor is to be construed as simply one component of a binding pair.

Ligands are the converse of receptors. While ligands are ordinarily low molecular weight organic compounds they are defined for the purposes of this invention as one component of a binding pair with a receptor in which they may be larger or smaller than the receptor.

Labelled ligand analogues are derivatives of ligands which carry a detectable substituent such as an enzyme, radioisotope or other known label but which are recognizable by and bind to a receptor for the parent ligand with approximately the same affinity as exhibited by the parent ligand.

A ligand-receptor pair is by definition reversibly bindable, i.e., its behavior is governed by the law of mass action. As a practical matter this means that either component of the ligand-receptor pair is displaceable by structurally related substances under the conditions normally encountered in specific binding assays, i.e., mild pH and the temperature and moderate ionic strength. Generally, the ligand-receptor pair will exhibit an affinity constant of greater than $10^7$ liters/mole, although useful results may be achieved well outside of this range.

Double receptor, specific binding assays have as their salient feature a first receptor specific for a second receptor, the second receptor ordinarily capable of binding a ligand. This ligand is generally the substance which is being determined in the assay, although it is possible that a third or more receptors may be positioned intermediate to the second receptor and ligand to be assayed. The ligand to be determined is hereinafter designated to be the sample ligand. In the usual context a ligand to be determined is first bound by its receptor, and in turn that receptor is bound by a second receptor. This seeming redundancy has considerable benefit in the analytical arts. The double receptor has been employed in at least three different techniques with the object of improving the separation of sample ligand from solution and simplifying reagent preparation. The first technique is herein termed the universal label method. Many specific binding assays use a labelled receptor in a direct assay, for example the well known sandwich immunoassays. In such methods an excess of insolubilized sample ligand receptor is incubated with a polyepitopic sample until a predetermined proportion of the sample is bound. The insoluble material is then washed and another sample ligand receptor is added. After an additional washing still another receptor is added, this receptor being specific for the second receptor rather than sample ligand. Also, it is labelled with a tag such as a radioisotope, enzyme, stable free radical or other known label so that the extent of its binding to the insoluble complex can be determined. Once again the insoluble material is washed. The amount of labelled second receptor remaining on the insoluble phase or separated in the washing is directly proportional to the amount of sample ligand bound to the ligand receptor and hence is proportional to the concentration of ligand in the sample. Where the last receptor to be added is an antibody, it is conventional to simply use the gamma globulin of a first animal species raised against the gamma globulin of a second, with the latter containing the anti-sample ligand activity. Since this gamma globulin will bind all antibodies from the second species, whatever their specificity for sample ligand, it will serve in labelled form as a universal label, See Beck et al., "Biochem. J." 145:607 (1975). This method has also been previously modified to require only one washing step. As can be seen from the above discussion this technique is directed towards simplifying reagent preparation since only one labelled receptor is needed for the sample ligand receptor, hence all assays can be conducted with a single labelled component.

The two other groups of double receptor, specific binding assays have as their key feature an improvement in the insolubilization of sample ligand receptor, and hence of labelled complexes. One of these assays is disclosed in U.S. Pat. No. 4,092,408. The essence of this method is the use of an insolubilized pair of receptors in place of the previously employed single insoluble receptor in a competitive immunoassay. The method comprises insolubilizing a receptor for sample ligand receptor, sequentially adding sample ligand receptor, then a mixture of labelled sample ligand analogue and sample, followed by separation of the phases and determination of the distribution of labelled sample ligand analogue.

The third group of double receptor specific binding assays are closely related to the preceding method. Instead of supplying an insolubilized receptor for sample ligand receptor during the assay a soluble receptor capable of binding the sample ligand receptor is added to precipitate the same ligand receptor and any sample ligand or labelled sample ligand analogue that may be bound thereto. This technique may be used in a competitive assay, in which case labelled sample ligand analogue is added along with the sample, in a sandwich assay where labelled sample ligand receptor is employed as described above after the sample ligand receptor has been permitted to bind the sample ligand, or in any other conventional system where a sample ligand receptor is a component. Precipitation may be aided by preaggregation of the receptor for sample ligand receptor or by immobilization or absorption of the receptor for sample ligand receptor on an insoluble support. This third group has been traditionally referred to as the double antibody method of phase separation. It is particularly desirable in that it does not affect the amount of labelled analogue which is bound to the sample ligand receptor since the assay is conducted with entirely water soluble reagents up until precipitation occurs.

The double receptor methods have suffered from a number of disadvantages and limitations, principally based on the fact that the affinity of such receptors for one another has been insufficient. This is manifested in requirements for relatively large plastic or solid surfaces for adsorption of receptor, making it particularly difficult to use in a coated tube, and for extensive and prolonged incubations, thus greatly extending the overall time required for completion of an assay. These low affinities are particularly critical where receptor or the antigen used to raise the sample ligand receptor is difficult to obtain.

These disadvantages have largely precluded the use of insoluble double receptors in automated rechargeable radioimmunoassay systems. These systems are characterized by the cyclical recharge of a conventional insoluble receptor after each assay by eluting the receptor-bound substances, e.g., sample ligand and labelled ligand analogue. These systems are handicapped particularly where large molecules such as antigens are to be determined. These molecules are less likely to penetrate to receptor sites hidden in a carpet of receptor spread across the insoluble surface. This results in low sample ligand receptor affinity and in turn a requirement for larger absorption area or longer reaction times. This clearly presents a severe problem when speed and sensitivity are paramount.

Furthermore, such rechargeable systems are rarely completely rechargeable, i.e., it is difficult to achieve complete elution of sample ligand or labeled sample ligand analogue, particularly where the receptor binding site is amphoteric. Further, while eluting reagents containing salts and extreme pH may remove ligands they will also gradually irreversibly denature the receptors, thereby making them unfit for reuse.

Accordingly, it is an object of this invention to supply a readily rechargeable receptor for automated specific binding assays.

It is an additional object to provide a labelled universal receptor having improved affinity.

It is a further object to improve the affinity of double receptor, specific binding assays for sample ligands.

It is also an object to accelerate phase separations in double receptor assays.

It is another object to reduce the surface area needed for double receptor assays to bind sufficient sample ligand.

Other objects of this invention will be apparent to those skilled in the art from a consideration of this specification taken in its entirety.

SUMMARY OF THE INVENTION

The above objectives are accomplished by using in place of the double receptors described above a complex having the structure $$A_{BL}(BL)_nA_1$$

wherein BL is a binding ligand, $A_{BL}$ is a receptor specific for said binding ligand, $A_1$ is a receptor, n is at least one, BL is covalently bound to $A_1$ and $A_{BL}$ is reversibly bound to BL.

DESCRIPTION OF THE PREFERRED EMBODIMENTS

The binding ligand BL is the salient feature of this invention. It is ordinarily selected from small molecules of molecular weight less than 1,000, preferably less than 400, which have superior ability to raise high titer, high affinity antibodies in mammals. It may also be one component of nonimmune, reversible binding system, e.g., vitamin $B_{12}$, triiodothyronine, or folic acid. The suitability of a proposed binding ligand for use in this invention may be readily determined by the skilled artisan. For example, in the case of an immune system, the binding ligand may be covalently attached to a carrier protein such as bovine serum albumin and the product injected into an animal in accordance with the known methods or preparation of hapten antibodies. The same procedure may be then followed for a reference ligand such as fluorescein. If the antibody titer and its affinity for binding ligand approximate the titer and affinity obtained with fluorescein then the proposed ligand is satisfactory for use in this invention. Ordinarily a binding ligand-receptor pair should have an affinity constant of greater than $10^7$ liters/mole. Methods for determining receptor-ligand affinity are conventional in the art, both for immune and nonimmune specific binding systems.

A less severe test but an adequate one for use in selecting a binding ligand is that the ligand should demonstrate greater affinity for its receptor than the gamma globulin of one animal demonstrates for that of another animal against which it has been raised. The affinity of the binding ligand for its receptor is of primary importance; the higher the affinity of the receptor and binding ligand the more valuable is the binding ligand for use in this invention.

A large variety of high titer, high affinity binding ligands are already known and are suitable for use in this invention. Exemplary substances are fluorescein, dinitrobenzene, antigenic polysaccharides, and the naphthylamines, acridines and rhodamines. Fluorescein is preferred.

Many of these ligands may be bound to receptors under extremely mild conditions, conditions that result in far less loss of antibody titer than treatments such as radioiodination, coated tube absorption or covalent bonding to insoluble supports. Severe losses of antibody titer are intolerable where the antibody is difficult to prepare with high titer and affinity. This invention enables one to sacrifice the inexpensive, high titer and affinity binding ligand receptor for difficult to obtain antibody or receptor because the titer reduction caused by covalent attachment of binding ligand receptor may be made lower than that caused by insolubilization or radioisotopic labelling of the receptor.

Mixtures of binding ligands and their receptors may be used, whether or not the ligands are in turn bound to the sample or different sample ligand receptors. The former embodiment applies in assays for one sample ligand wherein a single receptor is employed; it is possible to label this receptor with a plurality of different binding ligands, which in turn are insolublized by providing a plurality of receptors for the ligands. The latter embodiment is a double receptor specific binding assay for each sample ligand in a mixture of different sample ligands. In such an assay the improvement comprises using a number of complexes of the structure:

$$A_{BL}(BL)_nA_1$$

which are equal in number to the number of different sample ligands and where BL is a binding ligand, $A_{BL}$ is a receptor specific for said binding, $A_1$ is a receptor directed against one of said sample ligands in said mixture, n is at least one, BL is covalently bound to $A_1$ and $A_{BL}$ is reversibly bound to BL, with the further proviso that each receptor directed against one of said sample ligands is covalently bound to a binding ligand which is different from that bound to any other receptor directed against another of said sample ligands.

The binding ligand can be covalently bonded to the receptor $A_1$ via a variety of conventional linking groups. For example, in the case where fluorescein is used as the binding ligand there may be employed fluorescein isothiocyanate, dichlorotriazinyl aminofluorescein, or iodoacetyl aminofluoroscein, all of which can readily be covalently bonded to proteins, the first two to the protein amino groups and the last to the sulfhydryl groups. Analogous acridine compounds also can be covalently bonded to proteins. In the case of dinitrobenzene, there may be used 2,4-dinitrofluorobenzene. In the case of polysaccharides, such as purified bacterial wall antigens, the covalent bonding to the receptor can be accomplished by periodate oxidation of the polysaccharide, followed by the formation and subsequent reduction of the Schiff base. When using a naphthylamine as a binding ligand, dansyl chloride may be employed as the reactant with the receptor to form the conjugate.

The number and type of binding ligands conjugated to the sample ligand receptor will depend upon the size of the sample ligand receptor and the nature of its sample ligand binding site. Normally no more than 20, ordinarily 1 to 5 binding ligands will be conjugated to the sample ligand receptor. The larger the receptor the more binding ligands can be bonded without interfering with the binding of sample ligand. Additionally, binding ligands should not be conjugated at or near the sample ligand binding site. If the nature of the sample ligand site is unknown then the site may be protected by conducting the conjugation in the presence of an excess of sample ligand or by use of organic protecting groups. Furthermore, the binding ligands are selected and located such that any steric hindrance of the simultaneous binding of sample ligand and binding ligand receptor is minimized or eliminated, i.e., the binding ligands are located as far as possible from the sample ligand receptor epitopic sites so that sample ligand and binding ligand receptor may bind simultaneously. This parameter is usually optimized by routine experimentation.

Proportions of binding ligand ranging from about 2.5% to 50% by weight of the sample ligand receptor have been found to provide optimum results in the case of fluorescein, depending upon the particular receptor employed, but a considerably wider range can be used, from about 0.01 to 60% by weight not only of fluorescein but of other binding ligands as well.

$A_1$, the receptor to which the binding ligand is conjugated, is ordinarily any molecule which binds specifically and reversibly with the sample ligand desired to be assayed. Normally the receptor is a binding protein such as an antibody. In exceptional cases the receptor may be specific for other receptors which in turn ultimately bind sample ligand. When $A_1$ is an antibody it can be raised in conventional manner in a suitable animal by injecting antigenic ligand alone or, if the ligand is a hapten, covalently bonded to an antigenic protein. Nonimmune sample ligand receptors can be isolated from various sources, and many such binding proteins are commercially available. For example, intrinsic factor, a binding protein for the sample ligand Vitamin $B_{12}$, is obtainable from hog intestine and folate binding protein for the sample ligand folic acid is obtainable from reconstituted nonfat powdered milk. Many other binding proteins suitable for use in specific binding assays are known and can be used in the present invention, such as thyroxine binding globulin for assay of thyroxine in plasma, cortisol binding protein for assay of serum cortisol, and membrane associated specific receptor protein for assay of the peptide hormones such as ACTH.

$A_{BL}$, the binding ligand receptor, is preferably formed by raising an antibody against the binding ligand in any conventional manner. For example, the binding ligand can be covalently bonded to bovine serum albumin and used to raise an antibody in accordance with known practice. Where $A_{BL}$ is an antibody, the aminal used to raise $A_{BL}$ need not be different from the animal used to raise the sample ligand receptor. However, the animal should be selected for its ability to produce an antiserum of enhanced high affinity and high titer for the binding ligand. Binding ligand receptor is reversibly bound to the binding ligand in the $A_{BL}(BL)_nA_1$ complex, in contrast to the covalent bond between binding ligand and the sample ligand receptor. Such reversible bonds are well recognized in the art; they are conventionally formed by simply mixing the binding ligand and its receptor, and are thought to be based on hydrogen bonds and van der Waals forces. Their most distinguishing feature is that they should be governed by the law of mass action, albeit their equilibria in the case of this invention will optimally favor the bond rather than dissociation.

The binding ligand receptor will generally exhibit specific activity for a binding ligand which is different from the sample ligand. While it is possible for the sample ligand and binding ligand to be identical, the manufacture and use of a conjugate of sample ligand and sample ligand receptor will entail additional steps. In the case of manufacture, it is necessary to prevent the reactive sample ligand derivative from being covalently bound to the sample ligand receptor near or at the receptor's epitopic site, else the receptor will poorly bind sample ligand in use because of steric hindrance by the ligand. Yet the tendency of the sample ligand is to bind its receptor at just that point. However, this problem may be overcome by linking the ligand and its receptor while the receptor is bound to an insolublized matrix containing the ligand.

The use of the conjugate is also more difficult since it is not desirable to mix sample ligand and sample ligand receptor conjugate at the same time, as would be the case if sample ligand differed from biding ligand. Nonetheless, the foregoing embodiment falls within the scope of the invention even though it is not preferred.

It is ordinarily preferred that the binding ligand receptor be insolubilized, and that it be so prior to commencement of the assay. The sample ligand receptor may also be insolubilized before or during the conduct of a specific binding assay. This is not the case in receptor precipitation techniques described above where the purpose of the binding ligand receptor is to effect insolubilization after all components have reacted in solution. A technique for insolubilization is disclosed in U.S. Pat. No. 3,646,346 wherein a receptor solution is simply contacted with the wall of a plastic test tube until sufficient receptor is absorbed. Alternatively, the binding ligand receptor may be absorbed onto a particulate suspension. Also within the scope of this invention are receptors insolubilized by covalent crosslinking to insoluble matrices using well known techniques, e.g., protein insolubilization methods previously used with enzymes or antibodies, or by aggregation using either precipitants such as polyethylene glycol or cross-linking agents such as glutaraldehyde. Combinations of these methods may be used as well. For example, aggregate receptors may be absorbed onto plastic test tube walls.

The complex of this invention may be used in all of the known double receptor, specific binding assays described above as well as in two other methods which may be improved by use of the complex. These methods are affinity chromatography and rechargeable specific binding assays.

Affinity chromatography is a well known technique for purifying substances such as enzymes, antibodies, antigens and blood protein fractions from contaminated solutions. For example, see Cuatrecasas et al., "Annual Review of Biochemistry," volume 40, page 259 (1971) and U.S. Pat. No. 3,842,061. This technique comprises insolubilizing a binding partner of the desired substance; passing the contaminated solution over the insoluble binding partner; washing the bound, insolubilized substance; and then eluting the bound substance, for example by altering the pH or ionic strength. Affinity chromatography suffers from the defects noted above for specific binding assays, i.e., low affinity between insolubilized binding partner and its soluble binding substance, and difficulty in separation of the bound substance from the insoluble affinity matrix. Use of the complex of this invention improves separation efficiency. Also, removal of the aggregate of desired substance and binding ligand conjugate from the insolubilized binding ligand receptor is simplified by binding ligand displacement upon addition of an excess of binding ligand to the aggregate. The desired substance may then be readily separated from its receptor by dialysis or the like.

The capacity to conduct multiple, conventional, specific binding assays using a contiguous insoluble matrix, whether in a continuous flow or a batch system, is greatly enhanced by the complex of this invention. A distinguishing feature of such assays is that they are conducted in the same container; the assays may be separable or distinguishable by the use of different radioisotopes which can be discriminated from one another, e.g., $^{57}Co$ and $^{125}I$, (U.S. Pat. No. 3,952,091), or by removal of a subcomponent of the apparatus having one of the receptors bound to each subcomponent. Such subcomponents may be strips or tabs adherent to the interior of test tubes. The present invention eliminates the considerable inconvenience in synthesizing sample ligand analogues with different labels and, in the case of radioimmunoassays, overcomes the inherent limitations on the number of radioisotopes that can be employed as practical labels. In particular the improved receptor complex of this invention has valuable utility in rechargeable specific binding assay systems.

Such systems are known, for example see U.S. Pat. Nos. 4,053,284 and 4,039,652. The improved kinetics of sample ligand absorption by its receptor which are afforded by this invention are of considerable advantage in continuous flow assays because the amount of receptor can be reduced or the flow rate increased. Additionally, since a single absorbent having the binding ligand receptor immobilized thereon can be used for all assays, it is not necessary to replace the absorbent every time a different determination is made. This is of particular advantage in automated equipment where it is often inconvenient to replace the sample ligand. Finally, specific elution of bound labelled sample ligand analogue is facilitated by readily reversible binding of the binding ligand-sample ligand receptor complex from binding ligand receptor; binding ligands may be chosen which are unbound upon slight changes in their environment, e.g., lowering the pH by 2. These slight changes will not irreversibly denature binding ligand receptor, unlike the previously employed harsh conditions such as pH 2.5.

An exemplary embodiment of a multiple rechargeable specific binding assay would use a coiled capillary tube, the inner surface of which is coated with absorbed rabbit antibody to fluorescein. A method for sequential assay of vitamin $B_{12}$ and triiodothyronine would comprise passing solutions containing the following reagents through the tube in the stated order, with each solution optimally followed by a dilute saline or water wash: (1) Fluorescein-intrinsic factor conjugate, (2) a mixture of test sample and $^{57}Co$ labelled vitamin $B_{12}$, (3) weak acetic acid, (4) fluorescein-triiodothyronine antibody, (5) a mixture of test sample and $^{125}I$ labelled triiodothyronine, and (6) weak acetic acid. Standards and controls would be cycled in the same manner. One may determine either the eluted radioactivity or that retained in the tube after each passage of labelled sample ligand. The retained radioactivity may be determined by placing a suitable radiation counter in the vicinity of the coiled capillary. Reagents 1 and 2 may be combined before passage through the capillary, as may reagents 4 and 5.

Alternatively, it may be more convenient to absorb a mixture of fluorescein receptor and dinitrobenzene receptor on the inner wall of the capillary, pass a mixture of test sample, $^{57}Co$ labelled vitamin $B_{12}$, $^{125}I$ labelled triiodothyronine, fluorescein-intrinsic factor conjugate and dinitrobenzyl-triiodothyronine antibody conjugate through the capillary, wash the capillary, pass a water solution of fluorescein through the capillary, measure the radioactivity of the wash solution, pass a water solution of dinitrobenzene through the capillary and measure the radioactivity of the wash solution. Instead of counting the wash solution the reduction in radioactivity of the capillary as each binding ligand is passed therethrough may be determined. In both of the above examples the presence of two different labels is incidental; the method would work equally well with other assays in which $^{125}I$ is the sole label.

Turning to the three conventional double receptor, specific binding assays to which the improvements of this invention are most adaptable it should be noted that the concentrations of reagents, incubation times and other operating parameters of the assays are largely unaffected by the use of the inventive double receptor. Such minor modifications as need be done to optimize the determinations are well within the skill of the ordinary artisan.

In the improved universal label technique for polyepitopic sample ligands the inventive complex is used with labelled binding ligand receptor in place of a conjugate of gamma globulin and labelled anti-gamma globulin. A typical assay would comprise the steps of providing an insoluble sample ligand receptor, contacting this receptor with sample so that any sample ligand or a proportionate quantity thereof is absorbed onto its insoluble receptor, washing the insoluble material, then contacting it with a conjugate of a binding ligand to sample ligand receptor so that, in effect, the quantity of absorbed sample ligand becomes labelled with binding ligand, washing and finally contacting the insoluble material with binding ligand receptor which is labelled with a directly detectable substance, e.g., enzyme, radioisotope or stable free radical. Standards and controls are treated in the same fashion. The washing steps are optional although they are to be preferred for the most reproducible and sensitive results. In this connection, the addition of sample, conjugate and labelled binding ligand receptor can all be accomplished in one step. However, it is preferred that the labelled complex be added after the sample has been bound and washed free of the insoluble sample ligand receptor. The sample ligand receptor may be insolubilized after completion of the reaction.

Those assays which use a double receptor as an insolubilization aid have the binding ligand receptor bound to or absorbed on an insoluble support, or the binding ligand receptor insolubilizes the binding ligand-sample ligand receptor conjugate upon binding thereto. This phase separation step is merely an adjunct to the core of the assay. Thus the complex of this invention may be used in concert with any specific binding assay, competitive or direct.

A typical double receptor, direct specific binding assay comprises contacting the complex of this invention with a sample thought to contain said sample ligand whereby sample ligand present is absorbed by said conjugate, washing said complex, contacting said complex with labelled sample ligand analogue, washing the complex and determining the amount of residual bound or unbound labelled receptor.

A representative double receptor, competitive specific binding assay comprises simultaneously contacting the complex of this invention with labelled sample ligand analogue and with a sample thought to contain said sample ligand, whereby said sample ligand and said labelled sample ligand analogue competitively bind to the complex in proportion to their concentrations in solution, washing the complex and determining the amount of residual bound or unbound labelled sample ligand analogue.

Double receptor, specific binding assays of the sandwich type comprise contacting the complex of this invention with a sample thought to contain said sample ligand whereby said sample ligand present is absorbed by said complex, contacting said absorbed sample ligand with an excess of labelled receptor for said sample ligand, washing the complex, and determining the amount of residual bound or unbound labelled receptor.

The enhanced sandwich method of this invention is particularly advantageous in the determination of antigens thought to be indicative of hepatitis, referred to herein as hepatitis associated antigen. A savings of pipetting and washing steps over the previously used sandwich assays are obtained. The prior methods for hepatitis associated antigen determination comprise providing an insoluble surface coated with antibody to hepatitis associated antigen, contacting the surface with a test sample, washing the surface, contacting the surface with labelled antibody to hepatitis associated antigen, washing the surface and determining the distribution of labelled antibody between the soluble and insoluble phases. The improved method of this invention comprises employing in place of the insoluble surface coated with antibody to hepatitis associated antigen a complex of the formula:

$$Q—A_{BL}(BL)_nA_1$$

wherein Q is an insoluble support, BL is a binding ligand, $A_{BL}$ is a receptor for BL, n is at least 1 and $A_1$ is antibody to hepatitis associated antigen. When using this complex it is preferred to combine the heretofore sequential steps of contacting the insoluble surface with sample and with labelled antibody to hepatitis associated antigen, thus eliminating washing and pipetting steps.

Those prior art specific binding assays which use a labelled receptor as detectant, e.g., the sandwich assay described above, may additionally be combined with the universal receptor method. In this case, however, it is advisable for the binding ligand used in the insoluble sample ligand receptor complex to be different from that used in the labelled sample ligand receptor complex.

The particular operating parameters and methods for preparation of conventional reagents such as buffers used in the known specific binding assays described above may also be used with the inventive complex. For example, methods for preparation of insoluble receptors, e.g., antibodies, are well known, as are suitable labelled sample ligand analogues. Minor modifications in reaction conditions are well within the skill of the ordinary artisan and do not need to be belabored here.

Ordinarily the inventive methods and compositions herein will be embodied in kits. A competitive specific binding assay, for example, will generally be available commercially in a kit containing labelled analogue to the sample ligand; buffers; a complex comprising a binding ligand receptor and a receptor specific for the sample ligand covalently coupled to a binding ligand, the complex being capable of binding in solution simultaneously to both the sample ligand and labelled analogue; and means for insolubilizing the bound combination of the complex, sample ligand and sample ligand analogue. The insolublization means can be a plastic surface, for example in the form of a tube of polypropylene, polystyrene, or other suitable plastic which is used as a test tube for carrying out the assay and to the inner surface of which the receptor for the binding ligand is adsorbed. It can also be a particulate water-insoluble solid such as polysaccharide, for example, dextran, or glass beads, to which the receptor for the binding ligand is convalently bounded by conventional procedures. The insolubilizing means also can be a reagent such as polyethylene glycol, used to selectively preaggregate the receptor for the binding ligand; in this case it is also desirable to use in addition a carrier protein neutral to the reaction, e.g., gamma globulin, to which the binding ligand and preaggregated receptor have been coupled, as by covalent bonding. This preaggregated material assists in the insolublization of the bound combination. The kits will ordinarily include separate aliquots of the binding ligand receptor and the binding ligand-sample ligand receptor conjugate, although they may be combined into a single reagent. The relative proportions of binding ligand and of receptor for the sample ligand in the conjugate can be varied over a wide range. The coupling of binding ligands such as fluorescein to receptors such as antibodies or binding proteins, as for example by reacting fluorescein isothiocyanate with them, does not seriously affect the capability of the receptors to bind with their respective sample ligands until very large proportions, in some cases well over an equal weight, of binding ligand are coupled. The extent of decrease in binding capability with increase in proportion of bonding ligand will vary from one specific receptor to another as well as from each individual binding ligand to another. In each case, simple trial and error can be employed to determine the proportion or range of proportions which provide maximum binding of the conjugate to sample ligand while at the same time providing sufficient binding of the conjugate to receptor for binding ligand to ensure insolubilization.

The following specific examples are intended as illustrations but not limitations on the scope of the present invention.

EXAMPLE 1

A kit was provided for assay of Vitamin $B_{12}$ containing the following components:

1. Standard solutions containing known quantities of Vitamin $B_{12}$.
2. Solution of labelled analogue to Vitamin $B_{12}$ containing $^{57}Co$.
3. Buffer solution of glutamic acid.
4. Solution of conjugate of intrinsic factor coupled with fluorescein.
5. Rabbit fluorescein antiserum, treated and then preaggregated with polyethylene glycol.
6. Solution of carrier protein (bovine gamma globulin) coupled with fluorescein.

The standard solutions were prepared by addition of appropriate amounts of Vitamin $B_{12}$ to protein solutions containing 40 mg/ml Human Serum Albumin and 20 mg/ml bovine gamma globulin in phosphate buffered saline (10 mM potassium phosphate, 0.9% NaCl, 0.1% $NaN_3$, pH 7.4). This buffer is hereinafter referred to as "PBS." Final standards contained 2000, 1000, 500, 200, 100, 50 and zero pg $B_{12}$ per milliliter.

The solution of labelled analogue is a solution of cobalt-57 labelled Vitamin $B_{12}$ diluted such that 100 microliters contained approximately 10,000 counts per minute (approximately 30 pg).

The buffer solution referred to as component No. 3 above contained glutamic acid, gelatin and potassium cyanide in the amounts of 41 mMolar, 0.1% and 2.1 mMolar, respectively, at pH 3.5. This buffer serves to release compounds like Vitamin $B_{12}$ from specific binding proteins in the sample and to convert them to their cyano derivatives.

The solution of conjugate contained intrinsic factor covalently bonded by reaction with fluorescein isothiocyanate according to the following procedure. Into a test tube containing 1 ml of carbonate buffer (0.5M, pH 9.4) and 2 mg intrinsic factor was introduced 2 ml of carbonate buffer containing 1 mg fluorescein isothiocyanate. After stirring, the reaction mixture was allowed to stand overnight at room temperature. It was then applied to a 9 ml column (total bed volume) of polysaccharide (Sephadex G-25) in a 10 ml pipet, and equilibrated with PBS (25 mMolar phosphate). Elution with PBS yielded a single colored band eluting with the void volume. This was collected (0.3 mg/ml) and diluted 1:65 with PBS.

The rabbit fluorescein antibody was prepared by dissolving 1 g fluorescein isothiocyanate and 1 g bovine serum albumin in 30 ml of 0.5M carbonate buffer, pH 9.5 and allowing the reaction to proceed with gentle stirring at room temperature overnight. The mixture was then exhaustively dialyzed against PBS until no fluorescence was detected in the dialysate. The solution was lyophilized, and the solid administered to rabbits in Freund's adjuvant. Serum obtained from the rabbits containing fluorescein antibodies was partially purified by 40% ammonium sulfate saturation of the antiserum to precipitate immunoglobulins followed by resuspension of the precipitate in a volume of PBS equal to the original volume of the antiserum. This was preaggreagated by dilution 1:50 in PBS containing 6% polyethylene glycol 6000. The stirred suspension was allowed to equilibrate for at least one hour at room temperature before use.

The solution of carrier protein coupled to fluorescein was prepared by reacting fluorescein isothiocyanate with bovine gamma globulin at a molar ratio of 20:1 in 0.5M carbonate buffer at room temperature using the same procedure as that for preparing the fluorescein coupled to bovine serum albumin described above. The product was diluted 1:10 with PBS to provide a solution containing 3.5 mg/ml of protein.

The assay was carried out by introducing into separate 12×75 mm glass test tubes 0.5 ml each of the glutamic acid buffer solution and 0.1 ml each of standard solution of Vitamin $B_{12}$ or of unknown solution, as the case may be. After incubation at 100° C. for 20 minutes and cooling to room temperature, there is added to each tube 0.1 ml each of the solution of labelled analogue and 0.1 ml each of the solution of conjugate and the mixture was allowed to incubate at 37° C. for one hour. There was then added to each tube 0.1 ml of the solution of carrier protein coupled to fluorescein followed by 1.0 ml of the preaggreagated antifluorescein antibody and the mixture was further incubated for 20 minutes at 37° C. after which the tubes were centrifuged for 15 minutes at 5000 rpm. The supernatant was decanted and the precipitate pellets counted for residual radioactivity in a well gamma counter. Non-specific background count was measured in a similar tube containing all of the ingredients except the solution of conjugate.

The results were as follows for the standard solutions: Total Counts Per Minute Labelled Analogue Added = 11150

| Vitamin $B_{12}$, pg/ml | Counts per min. of ppte | Percent Bound based on total |
|---|---|---|
| 2000 | 1324 | 11.9 |
| 1000 | 1750 | 15.7 |
| 500 | 2250 | 23.3 |
| 200 | 2940 | 26.4 |
| 100 | 3270 | 29.3 |

-continued

| Vitamin $B_{12}$, pg/ml | Counts per min. of ppte | Percent Bound based on total |
|---|---|---|
| 50 | 3400 | 30.5 |
| 0 | 3700 | 33.2 |

Comparison of results of assays of human serum by the present invention with results obtained by conventional radioimmunoassay procedures showed satisfactory correlation.

EXAMPLE 2

A kit was provided for the assay of Vitamin $B_{12}$ in human serum containing components 1–4 each being similar to those of Example 1 but having the following differences. The glutamic acid buffer was replaced with a borate denaturation buffer, 0.05M sodium borate, 8 micrograms of KCN per milliliter, pH 9.3. This buffer denatures the Vitamin $B_{12}$ binding protein and frees the vitamin for assay. The solution of conjugate was prepared using fluorescein isothiocyanate at the weight ratio of 0.375/1 of intrinsic factor instead of 0.5/1, and the solution was diluted 1:500 instead of 1:65 with a buffer like PBS except that the 0.1% $NaN_3$ was replaced with 0.02% KCN, hereinafter referred to as PBS-KCN. The standard solutions were prepared using a solution of 7 grams per liter of human serum albumin in PBS-KCN. In place of components 5 and 6 of Example 1, there were provided coated tubes made as follows.

One-half ml of the resuspended ammonium sulfate precipitate of rabbit fluorescein antiserum prepared as in Example 1 was mixed with 400 ml of PBS at pH 6.0. The mixture was heated at 37° C. and to it was added 100 ml of a 2% glutaraldehyde solution in PBS pH 6.0, which had been heated to 37° C. prior to addition. This mixture was stirred at 37° C. for twenty minutes. Then to it was added 400 ml of a freshly prepared phosphate buffer 1.0M, pH 8.5, the mixture stirred, after which there was added 75 ml of a freshly prepared aqueous solution of sodium borohydride, 0.051M. The mixture was stirred for one-half hour at ambient temperature, then 250 ml of a freshly prepared 2.67% ascorbic acid solution in 1.0 Molar phosphate buffer at pH 8.5 was added. One milliliter of the resulting solution was placed in each of the desired number of 10×75 mm polypropylene test tubes and allowed to stand overnight at room temperature. The solution was removed from each tube by aspiration and each tube washed twice with 2 ml of 10 mM Tris buffer containing 1% gelatin and 0.01M EDTA at pH 7.5. The tubes were dried and stored at ambient temperature over dessicant until use.

The assay was carried out by first combining components 2 and 3 so that the borate denaturation buffer contained 30 pg of radioactive $B_{12}$ per 0.8 ml of buffer. A series of 12×75 mm glass test tubes was provided, each containing 0.8 ml of the mixture of components 2 and 3, and 0.1 ml of the appropriate standard solution or unknown solution as the case may be was then added to each tube. The tube was incubated at 100° C. for 45 minutes, then cooled to ambient temperature, and 0.1 ml of the solution of conjugate added. The content of each glass tube was decanted into one of the coated tubes, which was then incubated at 37° C. for 3 hours. After aspiration and washing twice with 2 ml of PBS, the tube was then counted for one minute on a gamma counter.

The results were as follows: Total Counts Per Minute Labelled Analogue Added = 10,600 Values represent averages of duplicate determinations.

| Vitamin $B_{12}$, pg/ml | Counts per min. of tube | Percent Bound based on total |
|---|---|---|
| 2000 | 630 | 5.9 |
| 1000 | 930 | 8.8 |
| 500 | 1492 | 14.1 |
| 200 | 2106 | 19.9 |
| 100 | 2447 | 23.0 |
| 50 | 2696 | 25.5 |
| 0 | 2741 | 25.9 |

EXAMPLE 3

A kit was provided for the assay of folic acid containing the following components:

1. Standard solutions of human serum containing known quantities of N-methyltetrahydrofolic acid and 5 mg/ml of ascorbic acid as preservative.
2. A lysine denaturation buffer.
3. A phosphate assay buffer. (PBS, as described in Example 1 or, preferably, 0.01M phosphate, 0.15M NaCl, EDTA and sodium azide at pH 7.3.).
4. A solution of labelled analogue to folic acid containing radioiodinated ($^{125}I$) pteroylglutamic acid.
5. Polypropylene tubes coated with fluorescein antibodies bound to a folate binding protein-fluorescein conjugate.

The serum standard solutions were commercially available preparations in a base of normal human serum which had been treated previously with charcoal to remove endogenous folic acid before known amounts of folic acid were re-added. The lysine denaturation buffer contained 0.007M lysine, 1 mg/ml ascorbic acid and had a pH of 10.5.

The solution of conjugate contained folate binding protein covalently bonded to fluorescein isothiocyanate which had been prepared in the following manner: 1 mg of commercially available affinity chromatography-purified folate binding protein mixture (Sigma), of which about 10% was folate binding protein, was dissolved in 0.1 ml of a 0.1M carbonate/bicarbonate buffer, pH 9.3. To this was added 250 micrograms of fluorescein isothiocyanate isomer I (Sigma) dissolved in 0.1 ml of the same carbonate buffer. The solutions were stirred in the dark at room temperature for 3 hours. Unreacted fluorescein isothiocyanate was removed from the protein fraction by passage of the reaction mixture through a Sephadex G25 column prepared in a 10 ml disposable serological pipet (5 ml bed volume). The Sephadex was swollen and the protein eluted from the column with phosphate buffer. The protein fractions from the chromatography column were pooled and diluted 1:3000 with buffer to give a stock solution containing 8.3 micrograms of protein/ml. Dilution should occur shortly before use because the conjugate is unstable upon dilute storage.

The polypropylene tubes coated with fluorescein antibodies bound to a folate binding protein-fluorescein conjugate were made in two steps. First the fluorescein antibody-coated tubes were made as disclosed in Example 2. Then 1 ml of phosphate buffer having 20, 40, 60 or 80 ng of the conjugate/ml was added to 20 tubes, the tubes allowed to stand overnight at room temperature in the dark, washed and dried. Then a standard curve was run as disclosed below to determine the optimal conjugate concentration on the basis of the standard curve midpoint, slope and maximum binding. 40 ng/ml of conjugate is ordinarily satisfactory. The conjugate-bound tubes were then prepared as disclosed above with the optimal conjugate concentration.

The assay was carried out by introducing into uncoated 12×75 mm polypropylene tubes 0.1 ml of the selected standard solution or unknown solution and 0.5 ml of the lysine denaturation buffer. The tube was then covered and incubated at 100° C. for 15 minutes, then cooled to ambient temperature. To the tube was then added 0.5 ml of phosphate buffer, pH 7.3, containing labelled folic acid analogue. The contents of this tube were mixed and transferred into a corresponding fluorescein antibody-conjugate coated polypropylene tube and this tube incubated at 37° C. for 90 minutes. After this time the tube contents were removed by aspiration and counted for 1 minute in a well gamma counter. It may be desirable to sequentially add the sample or standards tube and the labelled analogue to the fluorescein antibody-conjugate coated tube, separating the first addition from the second by a 15 minute incubation.

The results were as follows: Total Counts Per Minute Labelled Analogue Added=25986

| N-Methyl THFA ng/ml Serum | Counts per min. of tube | Percent Bound Based on Total |
|---|---|---|
| 30 | 3562 | 13.7 |
| 10 | 5876 | 22.6 |
| 4 | 7798 | 30.0 |
| 2 | 8348 | 32.1 |
| 0.8 | 9542 | 36.7 |
| 0.0 | 9163 | 35.2 |

EXAMPLE 4

A kit was provided for assay of triiodothyronine (T-3) containing the following components:

1. Standard solutions containing known quantities of T-3.
2. Solution of labelled analogue to T-3 containing $^{125}I$.
3. Buffer solution (PBS).
4. Solution of conjugate of T-3 antibody coupled to fluorescein.
5. Rabbit fluorescein antibody preaggregated as described in Example 1.
6. Solution of carrier protein coupled to fluorescein prepared as described in Example 1.

The solutions of components 1 and 2 were prepared by dissolving the active ingredients in PBS. Component 2 was prepared in a concentration such that 0.1 ml provided approximately 10,000 counts per minute.

The solution of conjugate was prepared by the same procedure used for preparing the conjugate of Example 1 except that a commercially available T-3 antibody was substituted for the intrinsic factor and the dilution of the eluted product (0.3 mg/ml) was 1:900 with PBS.

The assay was carried out by introducing into 12×75 mm glass test tubes 0.5 ml each of PBS and 0.1 ml of the selected standard or unknown solution. The remaining steps were carried out as described in Example 1, substituting the components of the present example for the corresponding components of Example 1.

The results were as follows for the standard solutions:

Total Counts Per Minute Labelled Analogue Added=10,400

| T-3 ng/ml | Counts Per Min. of ppte | Percent Bound Based on Total |
|---|---|---|
| 10 | 939 | 9.0 |
| 4 | 1185 | 11.3 |
| 1 | 2361 | 23.0 |
| 0.4 | 3076 | 29.0 |
| 0.1 | 3962 | 37.9 |
| 0 | 3961 | 37.9 |

EXAMPLE 5

A kit was provided for assay of T-3 containing components 1–4 identical to those of Example 4 except that the weight ratio in the conjugate was 0.1 mg fluorescein isothiocyanate per mg T-3 antibody and the dilution of the eluted conjugate product (0.3 mg/ml) was 1:334 with PBS. In place of components 5 and 6 of Example 4, there were provided coated tubes made as follows.

The resuspended rabbit antifluorescein antibody prepared as described in Example 1 was not preaggregated but instead was diluted with an equal volume of 80% saturated ammonium sulfate solution. The precipitate which formed was allowed to stand overnight at 4° C. then collected by centrifugation and resuspended in the same volume of PBS. This purified solution was then diluted 1:1000 with 0.5M phosphate buffer, pH 8.5. One ml of the diluted solution was placed in each of the required number of 10×75 mm polypropylene test tubes and allowed to stand overnight at room temperature. The solution was then removed from each tube by aspiration and the tube washed twice with 2 ml of 10 mM Tris buffer containing 1% gelatin, pH 7.4. The tubes were then dried and stored at 4° C. until use.

The assay was carried out by adding to each coated tube 1.0 ml PBS, 0.1 of the solution of labelled analogue, and 0.1 ml of the selected standard solution or unknown solution as the case may be. To this mixture was added 0.1 ml of the solution of conjugate. The tubes with their contents were incubated at 37° C. for one hour. The contents were then removed by aspiration, each tube washed twice with 2 ml of PBS, and the tubes were then counted.

The results were as follows for standard solutions:

Total Counts Per Minute Labelled Analogue Added=17,500

| T-3 ng/ml | Counts Per Min. per tube | Percent Bound Based on Total |
|---|---|---|
| 100 | 446 | 2.5 |
| 0 | 2009 | 11.8 |

In the case of each of Examples 1–4, the amount of sample ligand in the unknown could readily be determined by interpolation from a standard curve plotted from the results obtained with the standard solutions. In the case of Example 5, results obtained by using a few additional standard solutions would be desirable to bracket the desired range for improved accuracy.

I claim:

1. In a double receptor, specific binding assay for sample ligand wherein a first receptor is bound by a second receptor, the improvement comprising substituting for said double receptor a complex of the structure:

$$A_{BL}(BL)_nA_1$$

wherein BL is a binding ligand, $A_{BL}$ is an unlabelled receptor specific for said binding ligand, $A_1$ is a receptor, n is at least one, BL is covalently bound to $A_1$ and $A_{BL}$ is reversibly bound to BL.

2. The method of claim 1 wherein the complex is insoluble.

3. The method of claim 2 wherein the complex is insolublized by absorption of $A_{BL}$ onto an insoluble surface.

4. The method of claim 3 wherein said insoluble surface is the inner wall of a plastic test tube.

5. The method of claim 3 wherein said surface is polypropylene or polystyrene.

6. The method of claim 1 wherein $A_{BL}$ is preaggregated by precipitation with polyethylene glycol.

7. The method of claim 2 wherein $A_1$ is a receptor for said sample ligand.

8. The method of claim 7 wherein $A_1$ is a binding protein.

9. The method of claim 8 wherein $A_1$ is folate binding protein and the sample ligand is folic acid.

10. The method of claim 8 wherein $A_1$ is triiodothyronine antibody and the sample ligand is [triiodethyronine] *triiodothyronine.*

11. The method of claim 8 wherein $A_1$ is intrinsic factor and said sample ligand is vitamin $B_{12}$.

[12. The method of claim 8 wherein $A_1$ is an antibody and said sample ligand is an antigen.]

[13. The method of claim 1 wherein BL is a hapten having a molecular weight of less then 1,000 and an affinity constant of greater then about $10^7$ liters/mole.]

14. The method of claim 1 wherein BL is covalently bound to $A_1$ through an intermediate spacer molecule.

15. The method of claim 1 wherein BL is fluroescein, dinitrobenzene, a polysaccharide, a naphthylamine, an acridine or a rhodamine.

16. The method of claim 1 wherein $(BL)_nA_1$ is the reaction product of an antibody with fluorescein isothiocyanate.

17. The method of claim 1 wherein BL is fluorescein and $A_{BL}$ is fluorescein antibody.

18. The method of claim 7 further comprising contacting said complex with a sample thought to contain said sample ligand whereby said sample ligand present is absorbed by said complex, contacting said absorbed sample ligand with an excess of labelled receptor for said sample ligand, washing the complex, and determining the amount of residual bound or unbound labelled receptor.

19. The method of claim 7 further comprising contacting said complex with a sample thought to contain said sample ligand whereby sample ligand present is absorbed by said conjugate, washing said complex, contacting said complex with labelled sample ligand analogue whereby unoccupied residual sample-ligand binding sites in the complex bind said labelled sample ligand analogue, washing the complex and determining the amount of residual bound or unbound labelled receptor.

20. The method of claim 7 further comprising simultaneously contacting said complex with labelled sample ligand analogue and with a sample thought to contain said sample ligand, whereby said sample ligand and said labelled sample ligand analogue competitively bind to said complex in proportion to their concentrations in solution, washing the complex and determining the amount of residual bound or unbound labelled sample ligand analogue.

21. The method of claim 20 wherein said sample ligand is vitamin $B_{12}$, thyroxine, triiodothyronine, cortisol, folic acid or a peptide hormone.

22. In a double receptor, specific binding assay for sample ligand wherein a first receptor is bound by a second receptor to form a double receptor the improvement comprising substituting for said double receptor a complex of a formula:

$$Q—A_{BL}(BL)_nA_1$$

wherein Q is an insoluble support, BL is a binding ligand, $A_{BL}$ is a receptor for BL, n is at least one, $A_1$ is a receptor, BL is covalently bound to $A_1$, and $A_{BL}$ is reversibly bound to BL.

23. In a double receptor, specific binding assay for sample ligand wherein a first receptor is bound by a second receptor to form a double receptor, the improvement comprising substituting for said double receptor a complex of the formula:

$$A_{BL}(BL)_nA_1$$

wherein BL is a binding ligand, $A_{BL}$ is a receptor for BL, n is at least one, $A_1$ is a sample ligand receptor and BL is covalently bound to $A_1$.

24. In a method for determining hepatitis associated antigen comprising providing an insoluble surface coated with antibody to hepatitis associated antigen, contacting said surface with a test sample, washing said surface, contacting said surface with labelled antibody to hepatitis associated antigen, washing said surface and determining the distribution of labelled antibody between the soluble and insoluble phases, the improvement which comprises employing in place of said insoluble surface coated with antibody to hepatitis associated antigen a complex of the formula:

$$Q—A_{BL}(BL)_nA_1$$

wherein Q is an insoluble support, BL is a binding ligand, $A_{BL}$ is a receptor for BL, n is at least 1 and $A_1$ is antibody to hepatitis associated antigen.

25. A method for conducting sequential assays for more than one sample ligand which comprises (a) insolubilizing a number of different binding ligand receptors equal to the number of sample ligands to be assayed;

(b) absorbing onto said binding ligand receptors a plurality of conjugates, each conjugate comprising a binding ligand for which one of said binding ligand receptors is specific, covalently bound to a receptor for one of said sample ligands;

(c) adding test sample and a labelled sample ligand analogue or labelled sample ligand receptor;

(d) separating the insoluble phase;

(e) adding binding ligand to displace the conjugate containing that binding ligand;

(f) determining the amount of bound or displaced label; and (g) repeating steps (d) through (f) for each conjugate.

26. The method of claim 25 wherein the different binding ligand receptors are insolubilized on a plurality of contiguous insoluble surfaces.

27. The method of claim 25, wherein the binding ligands are fluorescein, dinitrobenzene, a polysaccharide, a naphthylamine, an acridine or a rhodamine.

28. The method of claim 25 wherein labelled sample ligand receptor is added.

29. The method of claim 25 wherein the different binding ligand receptors are mixed and then insolubilized on a capillary surface.

[30. A composition comprising a complex of the formula:

$$Q—A_{BL}(BL)_nA_1$$

wherein Q is an insoluble support, BL is a binding ligand, $A_{BL}$ is a receptor for BL, n is at least one, $A_1$ is a receptor, BL is covalently bound to $A_1$ and $A_{BL}$ is reversibly bound to BL.]

31. A composition useful for assaying a sample ligand, comprising a complex of the formula:

$$A_{BL}(BL)_nA_1$$

wherein BL is a binding ligand, $A_{BL}$ is a receptor for BL, n is at least one, $A_1$ is an antibody, BL is covalently bound to $A_1$, and $A_{BL}$ is reversibly bound to BL.]

[32. The composition of claim 31 wherein $A_{BL}$ is absorbed onto an insoluble support.]

[33. The composition of claim 32 wherein BL is a hapten having a molecular weight of less than about 1,000.]

[34. The composition of claim 33 wherein BL is fluorescein, dinitrobenzene, a polysaccharide, a naphthylamine, an acridine or a rhodamine.]

[35. The composition of claim 33 wherein BL is from about 0.01 to 60% by weight of $(BL)_nA_1$.]

[36. The composition of claim 31 wherein $A_{BL}$ is unlabelled.]

[37. The composition of claim 31 wherein $A_1$ is specific for the sample ligand.]

38. An insoluble surface capable of binding hepatitis associated antigen which comprises a complex of the formula:

$$Q—A_{BL}(BL)_nA_1$$

wherein Q is an insoluble support, BL is a binding ligand, $A_{BL}$ is a receptor for BL, n is at least one, $A_1$ is a receptor for hepatitis associated antigen, and BL is covalently bound to $A_1$.

39. In a double receptor, specific binding assay for sample ligand wherein a first receptor is bound by a second receptor to form a double receptor, the improvement comprising substituting for said double receptor a complex of the structure:

$$A_{BL}(BL)_nA_1$$

wherein BL is a binding ligand, $A_{BL}$ is a labelled receptor specific for said binding ligand, $A_1$ is a receptor, n is at least one, BL is covalently bound to $A_1$ and $A_{BL}$ is reversibly bound to BL.

40. The method of claim 39 wherein n ranges from one to about ten.

41. The method of claim 39 which comprises providing an insoluble sample ligand receptor, contacting said receptor with a sample thought to contain said sample ligand; and contacting the sample ligand with the complex of claim 2.

42. In a double receptor, specific binding assay for each sample ligand in a mixture of different sample ligands wherein for each sample ligand a first receptor is bound by a second receptor, the improvement comprising using a number of complexes of the structure:

$$A_{BL}(BL)_nA_1$$

which are equal in number to the number of different sample ligands and wherein BL is a binding ligand, $A_{BL}$ is a receptor specific for said binding ligand, $A_1$ is a receptor directed against one of said sample ligands in said mixture, n is at least one, BL is covalently bound to $A_1$ and $A_{BL}$ is reversibly bound to BL, with the further proviso that each receptor directed against one of said sample ligands is covalently bound to a binding ligand which is different from that bound to any other receptor directed against another of said sample ligands.

43. The assay of claim 42 wherein the receptors specific for the binding ligands are insolubilized on a contiguous insoluble matrix.

44. The assay of claim 43 wherein the receptors directed against the sample ligands are allowed to bind said ligands in competition with labelled sample ligands.

45. The assay of claim 44 comprising the further step of eluting in turn each of the bound sample ligands and labelled sample ligands from the matrix by successively washing the matrix with a solution of the binding ligand used to bond each sample ligand receptor to its respective binding ligand receptor.

*46. A composition useful for assaying a sample ligand, comprising a complex of the formula:*

$$A_{BL}(BL)_nA_1$$

*wherein BL is a binding ligand, $A_{BL}$ is a receptor for said binding ligand, n is at least one, BL is covalently bound to $A_1$ and $A_{BL}$ is reversibly bound to BL, and $A_1$ is thyroxine binding globulin.*

*47. A composition useful for assaying a sample ligand, comprising a complex of the formula:*

$$A_{BL}(BL)_nA_1$$

*wherein BL is a binding ligand, $A_{BL}$ is a receptor for said binding ligand, n is at least one, BL is covalently bound to $A_1$ and $A_{BL}$ is reversibly bound to BL, and $A_1$ is cortisol binding protein.*

*48. A composition useful for assaying a sample ligand, comprising a complex of the formula:*

$$A_{BL}(BL)_nA_1$$

*wherein BL is a binding ligand, $A_{BL}$ is a receptor for said binding ligand, n is at least one, BL is covalently bound to $A_1$ and $A_{BL}$ is reversibly bound to BL, and $A_1$ is a membrane associated specific receptor protein.*

*49. A composition of claim 48 wherein $A_1$ is a membrane associated specific receptor protein for a peptide hormone.*

*50. A composition of claim 48 wherein $A_1$ is a membrane associated specific receptor protein for ACTH.*

*51. A composition useful for assaying a sample ligand, comprising a complex of the formula:*

$$A_{BL}(BL)_nA_1$$

*wherein BL is a binding ligand, $A_{BL}$ is a receptor for said binding ligand, n is at least one, BL is covalently bound to $A_1$ and $A_{BL}$ is reversibly bound to BL, and $A_1$ is a receptor for a peptide hormone.*

*52. A composition useful for assaying a sample ligand, comprising a complex of the formula:*

$$A_{BL}(BL)_nA_1$$

*wherein BL is a binding ligand, $A_{BL}$ is a receptor for said binding ligand, n is at least one, BL is covalently bound to $A_1$ and $A_{BL}$ is reversibly bound to BL, and $A_1$ is a receptor for ACTH.*

*53. A composition useful for assaying a sample ligand, comprising a complex of the formula:*

$$A_{BL}(BL)_nA_1$$

*wherein BL is a binding ligand, $A_{BL}$ is a receptor for said binding ligand, n is at least one, BL is covalently bound to $A_1$ and $A_{BL}$ is reversibly bound to BL, and $A_1$ is a receptor for a hepatitis associated antigen.*

*54. A composition of claim 53 wherein said receptor is an antibody.*

*55. In a double receptor, specific binding assay for sample ligand wherein a first receptor is bound by a second receptor, the improvement comprising substituting for said double receptor a complex of the structure:*

$$A_{BL}(BL)_nA_1$$

*wherein BL is a binding ligand, $A_{BL}$ is an unlabeled receptor specific for said binding ligand, $A_1$ is an antibody binding protein, n is at least one, BL is covalently bound to $A_1$, $A_{BL}$ is reversibly bound to BL, said sample ligand is an antigen, and said complex is insoluble.*

* * * * *